United States Patent
Jahnke et al.

(10) Patent No.: US 10,182,786 B2
(45) Date of Patent: Jan. 22, 2019

(54) MODEL AND SYSTEM FOR USE IN AN IMAGING TECHNIQUE

(71) Applicants: Paul Jahnke, Berlin (DE); Michael Scheel, Berlin (DE)

(72) Inventors: Paul Jahnke, Berlin (DE); Michael Scheel, Berlin (DE)

(*) Notice: Subject to any disclaimer, the term of this patent is extended or adjusted under 35 U.S.C. 154(b) by 0 days.

(21) Appl. No.: 15/915,191

(22) Filed: Mar. 8, 2018

(65) Prior Publication Data

US 2018/0192986 A1   Jul. 12, 2018

Related U.S. Application Data

(62) Division of application No. 14/948,404, filed on Nov. 23, 2015, now Pat. No. 9,924,919.

(30) Foreign Application Priority Data

Aug. 13, 2015   (DE) .................... 20 2015 104 282 U

(51) Int. Cl.
*G16H 50/50* (2018.01)
*A61B 6/00* (2006.01)
(Continued)

(52) U.S. Cl.
CPC .............. *A61B 6/583* (2013.01); *B33Y 50/00* (2014.12); *G01R 33/58* (2013.01); *G06F 19/00* (2013.01);
(Continued)

(58) Field of Classification Search
None
See application file for complete search history.

(56) References Cited

U.S. PATENT DOCUMENTS

| | | | | |
|---|---|---|---|---|
| 4,331,021 A | * | 5/1982 | Lopez .................... | A61B 8/587 73/1.86 |
| 5,841,835 A | * | 11/1998 | Aufrichtig ............. | A61B 6/583 378/207 |

(Continued)

FOREIGN PATENT DOCUMENTS

DE   102012205193   10/2013

OTHER PUBLICATIONS

Theodorakou, C. et al., A novel method for producing X-ray test objects and phantoms, *Phys Med Biol*, 79: 1423-1438, 2004.
(Continued)

*Primary Examiner* — Hoon Song
(74) *Attorney, Agent, or Firm* — Dinsmore & Shohl LLP

(57) ABSTRACT

The invention relates to a model for use in an imaging technique based on an interaction of the model with an electromagnetic radiation. The model comprises a plurality of volume elements. The interaction intensities of two neighboring volume elements are distinguishable by an imaging technique. The model comprises first volume elements made of a supporting material, and second volume elements are made of a supporting material and a contrast material and exhibit a higher interaction intensity with the electromagnetic radiation than the first volume elements because of the presence of contrast material. The second volume elements have been generated by a printing method. The invention further relates to a method for fabricating the model by 3D printing.

20 Claims, 3 Drawing Sheets

(51) Int. Cl.
    *G01R 33/58*   (2006.01)
    *B33Y 50/00*   (2015.01)
    *G06F 19/00*   (2018.01)
    *A61N 5/10*    (2006.01)
    *A61B 6/03*    (2006.01)
    *G09B 23/28*   (2006.01)
    *G16H 40/63*   (2018.01)

(52) U.S. Cl.
    CPC ........... *G09B 23/286* (2013.01); *G16H 50/50* (2018.01); *A61B 6/032* (2013.01); *A61N 2005/1076* (2013.01); *G09B 23/28* (2013.01); *G16H 40/63* (2018.01)

(56) References Cited

U.S. PATENT DOCUMENTS

| | | | |
|---|---|---|---|
| 6,231,231 B1* | 5/2001 | Farrokhnia | A61B 6/583 |
| | | | 378/204 |
| 2003/0122544 A1 | 7/2003 | Parker et al. | |
| 2006/0088140 A1* | 4/2006 | Fahrig | A61B 6/06 |
| | | | 378/154 |
| 2008/0219410 A1 | 9/2008 | Gunzert-Marx et al. | |
| 2010/0202001 A1 | 8/2010 | Miller et al. | |
| 2014/0312535 A1 | 10/2014 | Dikovsky et al. | |

OTHER PUBLICATIONS

Korte, C. et al., A printed image quality test phantom for mammography, *Br. J. Radiol*, 78: 746-748, 2005.

* cited by examiner

MODEL AND SYSTEM FOR USE IN AN IMAGING TECHNIQUE

REFERENCE TO RELATED APPLICATIONS

This application is a divisional of U.S. patent application Ser. No. 14/948,404, filed Nov. 23, 2015, which claims priority to German Patent Application No. 202015104282.5, filed Aug. 13, 2015, the entire content of both of which is incorporated herein by reference.

FIELD OF THE INVENTION

The invention relates to a model for use in an imaging technique based on the interaction of the model with an electromagnetic radiation.

BACKGROUND OF THE INVENTION

Phantom models are used, inter alia, in radiology and radiation therapy for calibration and validation of devices for conducting imaging techniques, for planning of radiation therapy treatment, and for training of medical staff. Therein, the phantom models are supposed to display the properties of human tissue with respect to the interaction with electromagnetic radiation as realistically as possible.

Phantom models are used with methods employing ionizing radiation (x-rays and radioscopy, computer-assisted tomography, therapeutic irradiation), for magnetic resonance tomography (MRT), and in ultrasound.

Therein an image of the phantom model, which is used for example for calibration or for quality control of the device, is generated using the respective imaging technique.

Simple geometric models exist, the purpose of which is not the exact simulation of a specific tissue, but which are primarily supposed to provide reliable material properties. Materials are normally used, which have interaction properties that hardly resemble human tissue.

Moreover, anthropomorphic models, which are supposed to simulate the anatomy, morphology, and tissue properties of the human body in the context of the respective imaging technique, are known in the art. Such models can be equipped with dosimeters for dose measurement and can be combined with simple geometric models.

In particular, anthropomorphic models for ionizing techniques have a broad area of application in dose calibration, validation, and reduction. Measurements using such phantoms verify computer models for therapy planning in radiation therapy. Computer-assisted tomography protocols are established and optimized based on phantom scans.

Currently most computer-assisted tomography users mainly use geometric models for dose calibration and therapy planning. However anthropomorphic models are also used with the aim of more precise calibration and therapy planning compared to geometric models.

Current anthropomorphic models according are made by laborious and expensive methods, wherein materials resembling human tissue are used. From these materials, organs are shaped and assembled, such that a part of the body (i.e. only the upper abdomen), or the whole torso/body can be simulated.

In addition, current anthropomorphic models display the real anatomy and interaction properties with electromagnetic radiation of the simulated body and organs only in an idealized manner. Since the individual sections of the anthropomorphic models are respectively replicated from only one homogeneous material, no heterogeneities, which are typically found in reality, exist within the organ model. Generally, only a limited number of tissues are simulated, for example lung, bone, and soft tissue.

Consequently, images generated by means of anthropomorphic models also deviate substantially from images of real patients. Therefore, calculations for dosimetry, protocol optimization, and device calibration are potentially subject to substantial sources of error. For instance in therapy planning using known phantom models, the exact radiation dose that a patient receives cannot be verified using patient individual phantoms.

An exact calculation of the administered radiation dose is especially important in the area of radiation therapy. In this application very high radiation doses are administered to tumor tissue, whereas surrounding tissue is supposed to be preserved. To this end technically sophisticated systems are available by now. The possibility however to empirically test the actual dose deposition in individual patients is lacking in radiation therapy.

In order to eliminate these uncertainties to obtain reliable measurement data and to test these empirically, a new generation of realistic phantoms is needed. The current methods of manufacture are unable to display the individual human anatomy accurately. In consequence a completely new approach for the manufacture of realistic models is necessary.

Radiation dense contrast agents are known, the functional principle of which is based on the high atomic number of the elements contained in the contrast agent, whereby a large number of electrons exists around the nucleus, which absorb the incoming electromagnetic radiation. In particular, these contrast agents are used in computer-assisted tomography and x-ray diagnostics.

In a publication, Theodoraku describes printing of geometric shapes and two-dimensional x-ray images of a real patient using a potassium iodide solution as a contrast material on paper (Theodoraku et al., *Phys. Med. Biol.*, 49 (2004), 1423-1438). Subsequently, two dimensional x-ray images of the printouts were generated.

Therein, sheets of paper were printed repeatedly in some cases in order to deposit a larger amount of contrast material. Since every individual sheet allows only a certain amount of printing events, sheets of paper imprinted with the same arrangement of contrast material were stacked on top of each other in some cases in order to achieve a higher radiation density of the model. No three-dimensional structures however were modelled using this method.

3D printing methods facilitate a fast and cost-efficient production of individualized products and therefore are utilized for example for the development of prototypes. The different 3D printing methods have in common that two-dimensional elements are stacked on top of each other in a specific arrangement and thereby give rise to a three-dimensional object. One of these methods is based on stacking of simple printing paper. Thereby, each individual sheet can be imprinted and for example cut by a laser, such that the desired shape and color of the object is generated in the end.

SUMMARY OF THE INVENTION

An objective of the invention is to provide a model for use in an imaging technique based on the interaction of the model with an electromagnetic radiation, particularly wherein the model is adapted to resemble the interaction of a human or animal body or a part thereof with an electromagnetic radiation as accurately as possible, and wherein the model is characterized by a low production cost.

A further objective of the invention is to provide a cost efficient method for manufacturing a model for use in an imaging technique based on the interaction of the model with an electromagnetic radiation, particularly wherein the model is adapted to resemble the interaction of a human or animal body or a part thereof with an electromagnetic radiation as accurately as possible.

This objective is attained by the subject matter of the independent claims. Embodiments of the invention are described in the dependent claims.

A three-dimensional model comprising a plurality of volume elements fs provided, wherein each volume element exhibits a defined interaction intensity with an electromagnetic radiation.

The defined interaction intensities are facilitated by providing defined portions of contrast material at defined positions of the three-dimensional model. For example, the model may comprise a plurality of layers of a supporting material, particularly paper, wherein each layer comprises a defined arrangement of portions of the contrast material.

In particular, portions of a contrast material can be applied to the layers by means of a printing method. Particularly, the layers can be stacked on top of each other, and optionally, neighboring layers of the stack can be connected, particularly glued, to each other.

Optionally, the model can be brought into a desired shape, particularly cut into a desired shape.

Advantages

By means of the present invention it is possible to provide especially realistic phantom models, which accurately display the three-dimensional distribution of the interaction intensities of a real human body with electromagnetic radiation.

Particularly, the layers of the model can be imprinted with distributions of contrast material, which resemble sectional images of a real patient generated by computer-assisted tomography. By stacking of the layers a model is generated, which results in a very similar image in a computer-assisted tomography scan compared to a real patient with all physiological and pathological details.

Therein the achievable resolution in representation of small structures and inhomogeneities of the patient tissue in the model is only limited by the resolution of the imaging technique and by the resolution of the template and the printing method in fabricating the model.

One advantage of a model according to the invention is the significantly faster and more cost efficient production compared to anthropomorphic models of the state-of-the-art.

Furthermore tissues of the human body, particularly a patient, can be displayed in smallest details and tissue inhomogeneities using the model according to the invention in contrast to known geometric and anthropomorphic models of the state-of-the-art, which allows a more precise calibration and validation of devices and higher safety in therapy planning for radiation therapy.

Moreover, a model according to the invention also allows completely new areas of application. For instance it was never possible to empirically test the actual dose in the patient in computer-assisted tomography or radiation therapy. This possibility is significantly improved by use of a model according to the invention with integrated dosimeters. Using this method dose deliveries can be determined more reliably, which could previously only be approximated by measurements using simplified phantoms and calculation models based thereon.

Furthermore models according to the invention can be used for simulation of surgical interventions, which are executed under fluoroscopy/radioscopy using computer-assisted tomography devices or conventional x-ray devices.

Wherever alternatives for single separable features are laid out herein as "embodiments", it is to be understood that such alternatives may be combined freely to form discrete embodiments of the invention disclosed herein.

BRIEF DESCRIPTION OF THE DRAWINGS

The invention is further illustrated by means of the following examples displayed as figures, from which further embodiments and advantages of the invention can be drawn. These examples are meant to illustrate the invention but not to limit its scope.

FIG. 2A shows a two-dimensional image and a first layer with a first portion of contrast material, the image including a first image structure, a second image structure and a third image structure;

FIG. 2B shows a model according to the invention comprising a stack comprising the first layer, and further layers, and wherein the layers are stacked on top of each other; and FIG. 2C shows a connected model according to the invention, wherein the model comprises a stack comprising the first layer and further layers, and wherein the layers are stacked on top of each other and wherein the stacked layers are connected.

FIG. 3A shows a cut model according to the invention and a computer-assisted tomography device;

FIG. 3B shows a computer-assisted tomography scan of the cut model; and

FIG. 3C shows a detailed view of the first scan layer with a first scan image, wherein the first scan image comprises a first, second and third scan image structure.

DETAILED DESCRIPTION OF THE INVENTION

Figure 1:
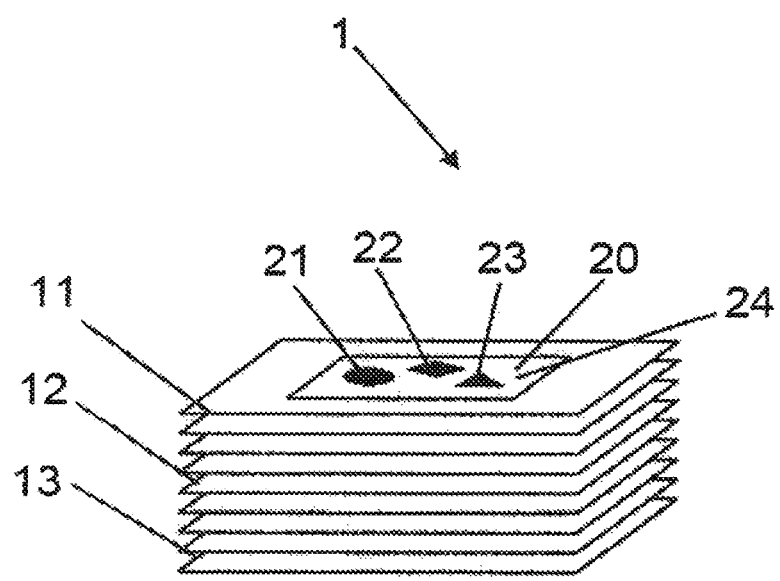
FIG. 1 shows a model according to the invention.

A first aspect of the invention relates to a model, particularly for use in an imaging technique based on the interaction of the model with an electromagnetic radiation. Therein the model comprises a plurality of volume elements, wherein a volume, a spatial position, and interaction intensity with an electromagnetic radiation is allocated to each of the volume elements. The interaction intensity relates to an electromagnetic radiation with a defined wavelength and radiation intensity from a defined source of radiation. The interaction intensities of two neighboring volume elements are distinguishable by means of an imaging technique.

The model comprises a plurality of first volume elements, and a plurality of second volume elements, wherein the first volume elements comprise a supporting material, and wherein the second volume elements comprise a supporting material and a contrast material, and wherein the second volume elements exhibit a higher interaction intensity with the electromagnetic radiation than the first volume elements by means of the contrast material, and wherein at least the second volume elements have been generated by a printing method.

In the context of the present specification, the term volume element is used in its meaning known in the art of mathematics and physics. The term volume element describes a partial volume of a body, wherein the total volume of the body can be at least approximately determined by addition of all volume elements.

In particular, the first volume elements may also comprise a contrast material. In particular, however, the second volume elements comprise a larger amount of contrast material than the first volume elements.

In the context of the present specification, the term electromagnetic radiation is used in its meaning known in the art of physics. Without any claim to completeness, electromagnetic radiation may comprise ionising radiation, particularly x-rays or gamma radiation, ultraviolet (UV) radiation, visible light, infrared radiation, microwaves, and/or radio waves.

In the context of the present specification, the term interaction is used in its meaning known in the art of physics. In the context used herein, the term interaction designates an interplay between an electromagnetic radiation and/or electromagnetic wave, with matter. In particular, this comprises absorption and scattering processes, or an excitation of a nuclear spin, wherein energy transported by the electromagnetic wave is taken up by an atom or molecule.

In the context of the present specification, the term imaging technique is used in its meaning known in the art of medicine, diagnostics, and equipment technology. The term designates a method, by means of which a plurality of data based on the interaction of an electromagnetic radiation with the matter of a human or animal body, is measureable, by means of which an image of the body can be generated or calculated. For example, imaging techniques comprise x-rays, computer-assisted tomography, or magnetic resonance tomography.

In the context of the present specification, the term contrast material describes a substance, which gives rise to a contrast in using an imaging technique, particularly a computer-assisted tomography method, based on an interaction of an electromagnetic radiation, particularly x-rays, with the substance, and wherein the substance is adapted to be applied onto a supporting material, or mixed with a supporting material. Therein, the imaging technique is based on the electromagnetic radiation. The term contrast material is not restricted to contrast agents used in medical diagnostics.

Therein, the contrast material comprises a defined interaction with the electromagnetic radiation.

In the context of the present specification, the term printing method describes a technical method for transmitting a contrast material to a supporting material, or for mixing the supporting material with the contrast material. In particular, printing methods comprise "ink jet printing" and "3D printing".

In certain embodiments, the volume of each of the second volume elements is smaller than 1 mm$^3$, particularly smaller than $1 \cdot 10^{-3}$ mm$^3$, more particularly smaller than $1.25 \cdot 10^{-4}$ mm$^3$, most particularly smaller than $8 \cdot 10^{-6}$ mm$^3$.

In particular, this corresponds to a cube having an edge length of less than 1 mm, particularly less than 0.1 mm, more particularly less than 0.05 mm, or even less than 0.02 mm.

In certain embodiments, the interaction intensity is a linear attenuation coefficient, or a computer-assisted tomography (CT) number, which particularly may be specified in Hounsfield units (HU).

Therein, the term Hounsfield units is used in its meaning known in the art of radiology. The term indicates a number, which is determined by calculating a difference by subtraction of the linear attenuation coefficient of water and the linear attenuation coefficient of a tissue, determining a value by dividing the difference by the linear attenuation coefficient of water, and multiplication of the value by 1000.

In the context of the present specification, the term linear attenuation coefficient is used in its meaning known in the art of physics. It designates a measure for the reduction of the intensity of an electromagnetic radiation while passing through a given material.

In certain embodiments, the first volume elements have also been generated by a printing method.

In certain embodiments, the first volume elements have been generated by a 3D printing method, wherein particularly also the second volume elements have been generated by a printing method.

In certain embodiments, the average interaction intensity of the first volume elements deviates from the average interaction intensity of the second volume elements by ≥1%, particularly ≤20%.

In certain embodiments, the model comprises a shape, wherein the shape is similar to a part of a human or animal body.

For example, this facilitates a use of the model for realistic simulation of surgical interventions, or for training of medical staff.

In certain embodiments, the imaging technique is a computer-assisted tomography method.

In certain embodiments, a model according to the invention can be utilized as a phantom model for calibration and quality control of a computer-assisted tomography device, or for simulation of a medical intervention using a computer-assisted tomography device, or for training of staff in operation of a computer-assisted tomography device.

In certain embodiments, the supporting material is arranged in layers, particularly of a thickness of 25-1000 µm, more particularly 50-500 µm, most particularly 80-500 µm.

In certain embodiments, the supporting material comprises cellulose, cotton, paper, and/or a foil, particularly wherein the foil comprises polyethylene terephthalate, cellulose acetate, polypropylene, polyurethane, polyethylene, or polyvinyl, with a weight portion of at least 0.01%.

The mentioned supporting materials are suitable to be imprinted with a contrast material.

In certain embodiments, the model comprises an essentially two-dimensional arrangement, namely an arrangement in a layer, of portions of a contrast material, wherein the contrast material comprises a defined interaction with the electromagnetic radiation, on which the imaging technique is based.

In certain embodiments, the essentially two-dimensional arrangement of portions of the contrast material may be generated by applying contrast material onto a layer of supporting material, particularly paper, by means of a printing method.

In certain embodiments, an essentially two-dimensional arrangement of portions of a contrast material is added to the supporting material, wherein the contrast material comprises a defined interaction with the electromagnetic radiation, on which the imaging technique is based.

In certain embodiments, the portions of contrast material are applied onto the supporting material, such that the supporting material carries the portions of contrast material.

In certain embodiments, the layers of supporting material are stacked on top of each other.

By stacking of layers of a supporting material, particularly sheets of paper, a three-dimensional model according to the invention may be easily fabricated.

In certain embodiments, neighboring layers of a stack of layers of the supporting material are connected, particularly glued, to each other.

Gluing the layers is advantageous, because the stability of a model according to the invention is increased in this manner.

In certain embodiments, the supporting material comprises a polymer, particularly a synthetic polymer.

In certain embodiments, the supporting material has been mixed with the contrast material.

In certain embodiments, the supporting material and the contrast material mixed with the supporting material may be mixed by means of a 3D printing method.

In certain embodiments, the contrast material exhibits a solubility of at least 5 $g \cdot l^{-1}$ at a temperature of 20° C. in a solvent, particularly water, ethanol, methanol, isopropanol, dimethyl sulfoxide, dimethyl formamide, or acetonitrile, most particularly water or ethanol.

In certain embodiments, the contrast material comprises a substance, particularly a salt, with a weight portion of at least 0.01%, wherein the substance exhibits a solubility in water or ethanol of 5 $g \cdot l^{-1}$ to 2000 $g \cdot l^{-1}$, particularly 100 $g \cdot l^{-1}$ to 1500 $g \cdot l^{-1}$, more particularly 200 $g \cdot l^{-1}$ to 1500 $g \cdot l^{-1}$, even more particularly 500 $g \cdot l^{-1}$ to 1500 $g \cdot l^{-1}$, most particularly 1000 $g \cdot l^{-1}$ to 1500 $g \cdot l^{-1}$, at a temperature of 20° C.

In certain embodiments, the contrast material comprises an element with an atomic number of ≥19, preferably iodine, lead, bromine, bismuth, stannic, antimony, gold, caesium, barium, rubidium, strontium, yttrium, zirconium, cerium, thorium, gadolinium, niobium, molybdenum, ruthenium, rhodium, palladium, silver, cadmium, indium, hafnium, or tantalum, more preferably iodine, lead, bismuth, caesium, barium, rubidium, strontium, or gadolinium, most preferably iodine, lead, bismuth, caesium, or gadolinium, with a weight portion of ≥0.01%.

In particular, substances comprising elements with an atomic number ~19 are used in x-ray diagnostics and computer-assisted tomography for contrast generation, since the interaction intensity of x-rays with atoms depends on the number of electrons of the atoms.

In certain embodiments, the contrast material comprises potassium iodide, sodium iodide, barium iodide, caesium iodide, caesium carbonate, caesium chloride, caesium fluoride, lead(ll) acetate, bismuth(lll) iodide, or strontium iodide, preferably potassium iodide, with a weight portion of ≥0.01%.

In particular, contrast agents containing iodine are administered to patients in x-ray diagnostics and diagnostics using computer-assisted tomography orally or intravenously, and are therefore readily available.

In certain embodiments, the contrast material comprises sodium chloride with a weight portion of ≥0.01%.

In certain embodiments, the contrast material comprises a glue with a weight portion of ≥0.01%.

Surprisingly it was found that structures of a model printed with glue as a contrast material can be visualized by means of a computer-assisted tomography method, wherein it was also surprising that the glue was printable by means of an inkjet printer.

In certain embodiments, the model comprises at least one cavity, wherein gas, particularly air, which is located in the cavity, exhibits a defined interaction with the electromagnetic radiation, on which the imaging technique is based.

A second aspect of the invention relates to a system comprising a model according to the first aspect of the invention, and a three-dimensional image of a body, particularly a human or animal body, wherein the three-dimensional image comprises a plurality of voxels, wherein each of the voxels comprises a spatial position, a volume, and a voxel intensity, and wherein the voxel intensity represents an interaction intensity of a body volume element of the body with an electromagnetic radiation measured by means of the imaging technique.

Therein, each volume element of the model is allocated to a voxel of the three-dimensional image, and the spatial position of each volume element of the model corresponds to the spatial position of the respective allocated voxel.

In certain embodiments, each volume element of the model has the same position as the allocated voxel, wherein the positions of the volume elements of the model refer to a first reference point, and the positions of the voxels refer to a second reference point, and wherein the position of the first reference point may differ from the portion of the second reference point.

In certain embodiments, the distance of each volume element from the first reference point may differ from the distance of the respective allocated voxel from the second reference point insofar as the distance of each volume element of the model from the first reference point can be derived by multiplication of the distance of the respective allocated voxel from the second reference point by a scaling factor.

In certain embodiments, the value of the scaling factor is 0.001 to 1000, preferably 0.01 to 100, more preferably 0.1 to 10, or even 0.5 to 2.

In the context of the present specification, the term human or animal body is used in its meaning known in the art of medicine. In addition to complete humans or animal bodies, the term human or animal body comprises parts of human or animal bodies, for example, but not exclusively, body parts, organs, or parts of organs.

In certain embodiments, the voxel intensity of the voxel is proportional to the interaction intensity of the interaction intensity of the respective volume element of the body measured by means of the imaging technique.

In certain embodiments, a voxel intensity may comprise at least one grey value or at least one color value of a voxel.

In certain embodiments, the three-dimensional image is a computer-assisted tomography image of a human or animal body, or a part thereof. Therein, particularly, the three-dimensional image consists of layers, wherein each layer comprises at least one two-dimensional image.

In certain embodiments of the system, the model comprises at least a first set of second volume elements and a second set of second volume elements, wherein the ratio of the average interaction intensity of the volume elements of the first set to the average interaction intensity of the volume elements of the second set deviates from the ratio of the average voxel intensity of the voxels allocated to the volume elements of the first set to the average voxel intensity of the voxels allocated to the volume elements of the second set by ≥200%, preferably ≤100%, more preferably ≤50%, even more preferably ≤20%, most preferably is 10%.

Therein, particularly, the plurality of volume elements may comprise any number of further sets of second volume elements, wherein the average interaction intensity of the second volume elements of each set measured by means of the imaging technique deviates from the average interaction intensity of the second volume elements of any other set measured by means of the imaging technique by ≥1%, preferably ≥5%, more preferably ≥10%, even more preferably ≥20%.

For example, the deviation between the interaction Intensity measured by means of the imaging technique and the average voxel intensity of a voxel is a result of measurement errors of the imaging technique, or inaccuracies in fabricating the model, particularly inaccuracies of a printing method.

In certain embodiments of the system, the interaction intensity of a volume element of the model measured by means of the imaging technique deviates from the average voxel intensity of the respective allocated voxel of the three-dimensional image by ≤200%, preferably ≤100%, more preferably ≤50%, even more preferably ≤20%, even more preferably ≤10%.

In certain embodiments of the system, each of the volume elements of the model comprises a portion of a contrast material, wherein the amount of contrast material in the portion is proportional to the voxel intensity of the voxel allocated to the volume element Therein the contrast material comprises a defined interaction with the electromagnetic radiation, on which the imaging technique is based.

A third aspect of the invention relates to a method for fabricating a model according to the first aspect of the present invention, wherein the model comprises a plurality of layers, and wherein the layers comprise a supporting material and a contrast material, wherein the contrast material exhibits an interaction with an electromagnetic radiation, which deviates from the interaction of the supporting material with the electromagnetic radiation, and wherein the model comprises a plurality of spatial positions.

Therein the method comprises applying a plurality of defined portions of the contrast material at a plurality of positions of the layers as a first step, and stacking the layers as a second step.

In certain embodiments, a first step of the method comprises generating a three-dimensional image, particularly from a plurality of sectional images of a human or animal body. Therein, using an imaging technique based on the interaction of components of the body with an electromagnetic radiation, a plurality of interaction intensities of the body with the electromagnetic radiation comprising a first plurality of positions is measured. From these measurements, a plurality of voxel intensities, particularly grey values or color values, of the three-dimensional image of the body comprising a second plurality of positions is generated, such that each interaction with a first position is allocated to a respective voxel intensity with a respective second position, and wherein each of the voxel intensities is proportional to the allocated interaction intensity.

In a second step, a plurality of portions comprising a defined amount of contrast material is applied at a third plurality of positions of the respective layer, such that the amount of contrast material at a third position is proportional to the voxel intensity at the respective second position.

In a third step of the method, the layers of supporting material are stacked in an arrangement, such that the interaction intensity of the portion of contrast material with the electromagnetic radiation at the third position essentially corresponds to the interaction intensity of the body with the electromagnetic radiation at the respective first position. Therein "essentially corresponds" is meant as "deviates by ≤200%, preferably ≤100%, more preferably ≤50%, even more preferably ≤20%, even more preferably ≤10%.

In certain embodiments, the method comprises fabricating a plurality of mixtures of a supporting material and a contrast material as a first step, wherein the contrast material exhibits an interaction with an electromagnetic radiation, which deviates from the interaction of the supporting material with the electromagnetic radiation. A second step of the method is generating a three-dimensional, preferably solid, structure from the plurality of mixtures.

In certain embodiments, at least one step of the method is executed by means of a 3D printer. Therein, preferably, a first supporting material is mixed with the contrast material. During the printing procedure, mixtures of the first supporting material with a second supporting material are prepared, and particularly arranged in layers. The amount of contrast material in a volume element of the 3D printed model is preferably derived from the grey value or color value of a 3D image to be printed, preferably of a scan image generated by means of the imaging technique.

Therein, particularly, the amount of contrast material in a volume element of the 3D printed model is proportional to the grey value or color value of the 30 image to be printed.

In certain embodiments, the method comprises applying a plurality of defined portions of the contrast material onto a plurality of layers, such that the amount of the contrast material in the portion at the third position is proportional to the voxel intensity at the respective second position as a first step, and stacking the layers as a second step.

In certain embodiments, at least one step of the method is executed by means of an inkjet printer. Therein the contrast material is filled into the cartridge of an inkjet printer, and is applied onto the supporting material during the printing procedure in a density, which preferably corresponds to the grey value or color value of an image to be printed, preferably a sectional image generated by means of the imaging technique. Therein, preferably, paper or textiles serve as supporting material.

In certain embodiments of the method, the model is brought into the shape, particularly cut into the shape of a part of a human or animal body.

In certain embodiments of the method, the imaging technique is a computer-assisted tomography method.

In certain embodiments of the method, each of the layers exhibits a thickness of 25-1000 µm, preferably 50-500 µm, most preferably 80-500 µm.

In certain embodiments of the method, the supporting material comprises cellulose, or paper, or a foil, particularly wherein the foil comprises polyethylene terephthalate, cellulose acetate, polypropylene, polyurethane, polyethylene, or polyvinyl, with a weight portion of at least 0.01%.

In certain embodiments of the method, the layers of supporting material are stacked on top of each other.

In certain embodiments of the method, neighboring layers of the supporting material are connected, particularly glued, to each other.

In certain embodiments, the model is fabricated by connecting, particularly gluing, plugging, or binding of at least two models.

Thereby, advantageously, scaling limitations of a printing method can be circumvented.

In certain embodiments of the method, a contrast material comprising a substance, which exhibits a solubility of at least 5 g·l$^{-1}$ at a temperature of 20° C. in a solvent, preferably water, ethanol, methanol, isopropanol, dimethyl sulfoxide, dimethyl formamide, or acetonitrile, most preferably water or ethanol, is used.

Thereby, the contrast material can be applied onto a supporting material from a solution by means of a printing method. Therein, the solvent serves as a carrier of contrast material, and is removed from the model by drying following the printing process.

In certain embodiments of the method, a contrast material comprising a substance, particularly a salt, with a weight portion of ≥0.01%, wherein the substance exhibits a solubility in water or ethanol of 5 g·l$^{-1}$ to 2000 g·l$^{-1}$, preferably 100 g·l$^{-1}$ to 1500 g·l$^{-1}$, more preferably 200 g·l$^{-1}$ to 1500 g·l$^{-1}$, even more preferably 500 g·l$^{-1}$ to 1500 g·l$^{-1}$, most preferably 1000 g·l$^{-1}$ to 1500 g·l$^{-1}$, at a temperature of 20° C., is used.

In certain embodiments of the method, a contrast material comprising an element with an atomic number of ≥19, preferably iodine, lead, bromine, bismuth, stannic, antimony, gold, caesium, barium, rubidium, strontium, yttrium, zirconium, cerium, thorium, gadolinium, niobium, molybdenum, ruthenium, rhodium, palladium, silver, cadmium, indium, hafnium, or tantalum, more preferably iodine, lead, bismuth, caesium, barium, rubidium, strontium, or gadolinium, most preferably iodine, lead, bismuth, caesium, or gadolinium, with a weight portion of ≥0.01%, is used.

In certain embodiments of the method, a contrast material comprising potassium iodide, sodium iodide, barium iodide, caesium iodide, caesium carbonate, caesium chloride, caesium fluoride, lead(ll) acetate, bismuth(lll) iodide, or strontium iodide, preferably potassium iodide, with a weight portion of ≥0.01%, is used.

In certain embodiments of the method, the contrast material comprises sodium chloride with a weight portion of ≥0.01%.

In certain embodiments of the method, the contrast material comprises glue with a weight portion of ≥0.01%.

In certain embodiments of the method, recesses are created in individual layers, preferably cut or left out from individual layers, during fabrication of the model, such that after assembly of the model, particularly by stacking, and/or connecting the layers, at least one cavity is created within the model.

The following further aspects and embodiments of the invention are described as items, which may also be formulated as claims.

Item 1: A method for fabricating a model according to the first aspect of the present invention, wherein the model comprises a plurality of layers, and wherein said layers comprise:
  a supporting material, and
  a contrast material, wherein said contrast material exhibits an interaction with an electromagnetic radiation, which deviates from the interaction of said supporting material with said electromagnetic radiation, and
  a plurality of spatial positions,
wherein the method comprises the following steps:
  applying a plurality of defined portions of said contrast material at a plurality of positions of said layers, and stacking said layers.

Item 2: The method according to item 1, comprising the following steps:
  generating a three-dimensional image, particularly from a plurality of sectional images of a human or animal body, wherein, using an imaging technique based on the interaction of components of said body with an electromagnetic radiation, a plurality of interaction intensities of said body with said electromagnetic radiation comprising a first plurality of positions is measured, a plurality of voxel intensities of a three-dimensional image of said body comprising a second plurality of positrons is generated, such that each interaction intensity with a first position is allocated to a respective voxel intensity with a respective second position, and wherein each of said voxel intensities is proportional to said allocated interaction intensity, and
  applying a plurality of portions comprising a defined amount of contrast material at a third plurality of positions of said layers, such that said amount of contrast material at said third position of said respective layer is proportional to said voxel intensity at said respective second position, and
  stacking said layers of supporting material in an arrangement, such that said interaction intensity of said portion of contrast material with said electromagnetic radiation at said third position essentially corresponds to said interaction intensity of said body with said electromagnetic radiation at said respective first position.

Item 3: The method according to item 1 or 2, wherein the method comprises the steps of:
  fabricating a plurality of mixtures of a supporting material and a contrast material, which exhibits an interaction with an electromagnetic radiation, which deviates from the interaction of said supporting material with said electromagnetic radiation, and
  generating a three-dimensional, particularly solid, structure from said plurality of mixtures.

Item 4: The method according to item 3, wherein at least one step of the method is executed by means of a 3D printer.

Item 5: The method according to item 2, wherein the method comprises the steps of:
  applying a plurality of defined portions of said contrast material onto a plurality of layers, such that the amount of said contrast material in said portion at said third position is proportional to said voxel intensity at said respective second position, and
  stacking said layers.

Item 6: The method according to item 5, wherein at least one step of the method is executed by means of an inkjet printer.

Item 7: The method according to any one of the items 1 to 6, wherein said model is brought into the shape, particularly cut into the shape of a part of a human or animal body.

Item 8: The method according to any one of the items 1 to 7, wherein said imaging technique is a computer-assisted tomography method.

Item 9: The method according to any one of the items 1 to 8, wherein each of said layers exhibits a thickness of 25-1000 μm, particularly 50-500 μm, more particularly 80-500 μm.

Item 10: The method according to any one of the items 1 to 9, wherein said supporting material comprises cellulose, paper, or a foil.

Item 11: The method according to any one of the items 1 to 10, wherein said layers of said supporting material are stacked.

Item 12: The method according to any one of the items 1 to 11, wherein neighboring layers of said supporting material are connected, particularly glued, to each other.

Item 13: The method according to any one of the items 1 to 12, wherein said model (1) is fabricated by connecting, particularly gluing, plugging, or binding of at least two models (1) according to the invention.

Item 14: The method according to any one of the items 1 to 13, wherein a contrast material comprising a substance, which exhibits a solubility of at least 5 g·l$^{-1}$ at a temperature of 20° C. in a solvent, particularly water, ethanol, methanol, isopropanol, dimethyl sulfoxide, dimethyl formamide, or acetonitrile, most particularly water or ethanol, is used.

Item 15: The method according to any one of the items 1 to 14, wherein a contrast material comprising a substance, particularly a salt, with a weight portion of ≥0.01%, wherein said substance exhibits a solubility in water or ethanol of 5 g·l$^{-1}$ to 2000 g·l$^{-1}$, particularly 100 g·l$^{-1}$ to 1500 g·l$^{-1}$, more particularly 200 g·l$^{-1}$ to 1500 g·l$^{-1}$, even more particularly 500 g·l$^{-1}$ to 1500 g·l$^{-1}$, most particularly 1000 g·l$^{-1}$ to 1500 g·l$^{-1}$, at a temperature of 20° C., is used.

Item 16: The method according to any one of the items 1 to 15, wherein a contrast material comprising an element with an atomic number of ≥19, particularly iodine, lead, bromine, bismuth, stannic, antimony, gold, caesium, barium, rubidium, strontium, yttrium, zirconium, cerium, thorium, gadolinium, niobium, molybdenum, ruthenium, rhodium, palladium, silver, cadmium, indium, hafnium, or tantalum, more particularly iodine, lead, bismuth, caesium, barium, rubidium, strontium, or gadolinium, most particularly iodine, lead, bismuth, caesium, or gadolinium, with a weight portion of ≥0.01%, is used.

Item 17: The method according to any one of the items 1 to 16, wherein a contrast material comprising potassium iodide, sodium iodide, barium iodide, caesium iodide, caesium carbonate, caesium chloride, caesium fluoride, lead(ll) acetate, bismuth(lll) iodide, or strontium, is used.

Specifically, FIG. 1 shows a model 1 according to the invention with a first layer 11, a second layer 12, and a third layer 13, wherein the first layer 11, the second layer 12, and the third layer 13 comprise a supporting material, and are part of a stack, wherein further layers are positioned between the first layer 11 and the second layer 12, and between the second layer 12 and the third layer 13. The first layer 11 comprises a first portion of contrast material 20, which covers a part of the surface of the first layer 11. The portion of contrast material 20 is distributed on the surface of the first layer 11, such that by means of different densities of the contrast material at different positions of the surface of the first layer 11 a first structure 21, a second structure 22, a third structure 23, and a background 24 are formed.

Therein the densities of the first structure 21, the second structure 22, and the third structure 23 differ from the density of the background 24, such that by means of an imaging technique, particularly a computer-assisted tomography method, the first structure 21, the second structure 22, the third structure 23, and the background 24 can be displayed as a result of the respective interaction intensities with an electromagnetic radiation, particularly x-rays.

The second layer 12 comprises a second portion of contrast material, wherein the second portion of contrast material is distributed on the surface of the second layer 12, such that by means of different densities of the contrast material at different positions of the surface of the second layer 12 structures and a background can be formed, wherein the densities of the structures differ from the density of the second background, such that the structures can be displayed by means of an imaging technique, particularly a computer-assisted tomography method.

In analogy, also the third layer, and optionally further layers comprise portions of contrast material and structures, such that in each layer structures can be displayed by means of the imaging technique.

Thus, for example a three-dimensional image of the model 1 can be constructed by means of the imaging technique, and optionally by means of further calculations.

Figures 2A, 2B, 2C:
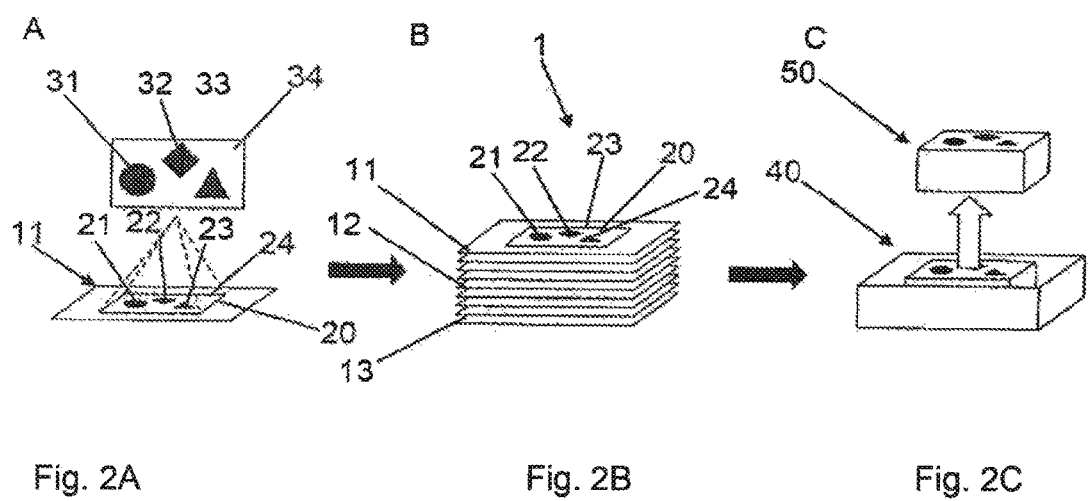
FIGS. 2A-2C show an example of a fabrication procedure for a model according to the invention.

Specifically, FIG. 2A shows a two-dimensional image and a first layer 11 with a first portion of contrast material 20. Therein the image comprises a first image structure 31, a second image structure 32, and a third image structure 33.

In particular, the two-dimensional image may have been generated by means of an imaging technique using an electromagnetic radiation, particularly by means of a computer-assisted tomography method, wherein the image displays the interaction intensities of a section of a human or animal body or a part thereof with the electromagnetic radiation. Particularly, the image may display different interaction intensities as different voxel intensities, particularly grey values, or color values.

The first layer 11 comprises a first portion of contrast material 20, wherein the first portion of contrast material covers a part of the surface of the first layer 11. The first portion of contrast material 20 is distributed on the surface of the first layer 11, such that by means of different densities of the contrast material at different positions of the surface of the first layer 11 a first structure 21, a second structure 22, a third structure 23, and a background 24 are formed. Therein, the first image structure 31 is represented by the first structure 21, the second image structure 32 is represented by the second structure 22, and the third image structure 33 is represented by the third structure 23. For example, the first portion of contrast material 20 can be applied onto the first layer 11 by a printing method, wherein for example the cartridge of an inkjet printer is filled with a contrast material, such that the contrast material can be applied onto the first layer by means of the printer.

Specifically, FIG. 2B shows a model 1 according to the invention, wherein the model 1 comprises a stack comprising the first layer 11, and further layers, and wherein the layers are stacked on top of each other.

Specifically, FIG. 2C shows a connected model 40 according to the invention, wherein the model comprises a stack comprising the first layer 11 and further layers, and wherein the layers are stacked on top of each other, and wherein the stacked layers are connected, particularly glued. Furthermore, FIG. 2C shows a cut model 50 according to the invention, wherein the cut model 50 constitutes a part of the connected model 40, and wherein the cut model 50 has been generated from the connected model 40 by a cutting procedure.

Figures 3A, 3B, 3C:
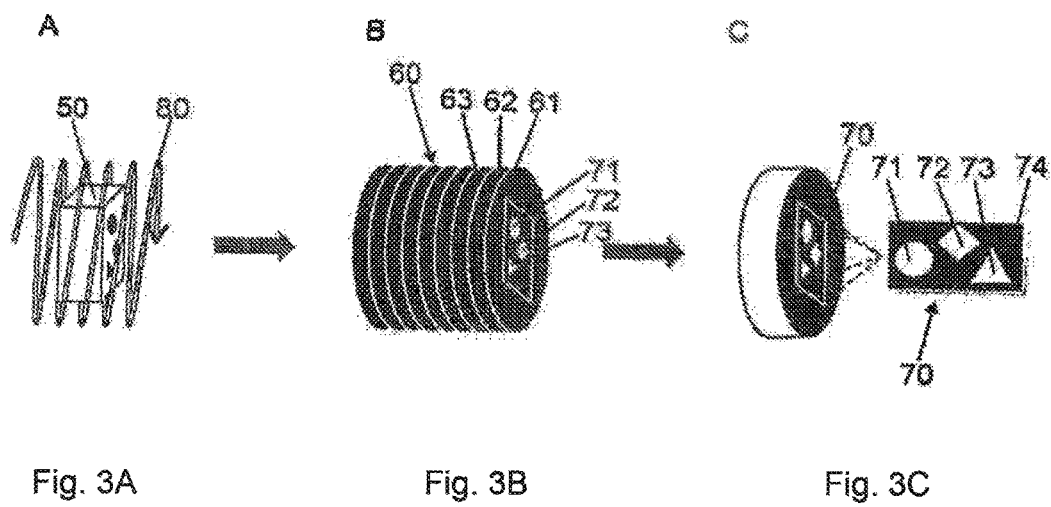
FIGS. 3A-3C show an application example for a model according to the invention.

Specifically, FIG. 3A shows a cut model 50 according to the invention and a computer-assisted tomography device 80, wherein the model 50 is arranged in the computer-assisted tomography device 80, such that a computer-assisted tomography scan of the model 50 can be generated by means of the computer-assisted tomography device 80, such that the interaction intensities of the volume elements of the cut model 50 with x-rays can be displayed by means of the computer-assisted tomography scan by means of the computer-assisted tomography device 80.

Specifically, FIG. 3B shows a computer-assisted tomography scan 60 of the cut model 50, wherein the scan 60 comprises a first scan layer 61, a second scan layer 62, and a third scan layer 63. Therein each of the layers represents the interaction intensities of one or several layers of the model 50.

Specifically, FIG. 3C shows a detailed view of the first scan layer 61 with a first scan image 70, wherein the first scan image 70 comprises a first scan image structure 71, a second scan image structure 72, and a third scan image structure 73.

Respectively, further scan image structures of the scan 60 not shown in FIG. 3A may represent further structures of the model 50 not shown in FIG. 3C. Therein, particularly, the scan structures of each scan layer represent the structures of one or several layers of the model 50.

For fabrication of a specific example of the invention, negative images of sectional images from a computer-assisted tomography scan of a patient were generated first. To this end, light grey values corresponding to high interaction intensities with x-rays of the computer-assisted tomography device were converted into dark grey values by inverting.

The negative images were then printed using a commercial inkjet printer, wherein a potassium iodide solution was filled into the cartridge of the inkjet printer. Commercial 80 g printing paper, or photographic paper of the strengths 105 g, 120 g, 150 g, 170 g, and 180 g were used.

The layers were stacked on top of each other and glued or connected by compression. Subsequently, the model was scanned using a computer-assisted tomography device.

Herein, the anatomy of the patient was displayed accurately and at high resolution. In particular, all details such as organ contours and tissue inhomogeneities, the entire variety of the tissues of the human body as well as pathological processes were displayed.

A model was also generated by imprinting textiles with a potassium iodide solution. The textile layers were subsequently stacked and sewed. Using the generated model, the periradicular therapy, a common CT intervention, could be successfully simulated by means of a computer-assisted tomography device.

For fabrication of further models, caesium containing, lead containing, and gadolinium containing aqueous solutions were used.

Furthermore, models were imprinted with commercial glue from natural product polymers, in part in combination with other contrast materials, wherein the glue served as a contrast material.

| List of Reference Signs | |
|---|---|
| Model | 1 |
| First layer | 11 |
| Second layer | 12 |
| Third layer | 13 |
| First portion of contrast material | 20 |
| First structure | 21 |
| Second structure | 22 |
| Third structure | 23 |
| Background | 24 |
| First image structure | 31 |
| Second image structure | 32 |
| Third image structure | 33 |
| Image background | 34 |
| Connected model | 40 |
| Cut model | 50 |
| Computer-assisted tomography scan | 60 |
| First scan layer | 61 |
| Second scan layer | 62 |
| Third scan layer | 63 |
| First scan image | 70 |
| First scan image structure | 71 |
| Second scan image structure | 72 |
| Third scan image structure | 73 |
| Scan image background | 74 |
| Computer-assisted tomography device | 80 |

The invention claimed is:

1. A model for use in an imaging technique based on an interaction of said model with an electromagnetic radiation, wherein said model comprises a plurality of volume elements, wherein each of said volume elements has a volume, a spatial position, and an interaction intensity with the electromagnetic radiation such that the interaction intensities of two neighboring volume elements are distinguishable by an imaging technique, and wherein said model comprises a plurality of first volume elements comprising a supporting material arranged in layers, and a plurality of second volume elements comprising a supporting material and a contrast material, and the volume of each of said second volume elements is <1mm$^3$, characterized in that said second volume elements exhibit a higher interaction intensity with said electromagnetic radiation than said first volume elements due to said contrast material.

2. The model according to claim 1, characterized in that said volume of each of said second volume elements is <1,25·10$^{-4}$ mm$^3$.

3. The model according to claim 1, characterized in that said volume of each of said second volume elements is <1·10$^{-5}$ mm$^3$.

4. The model according to claim 1, characterized in that said first volume elements have an average interaction intensity, said second volume elements have an average interaction intensity and the average interaction intensity of said first volume elements deviates from the average interaction intensity of said second volume elements by ≥1%.

5. The model according to claim 1, characterized in that said supporting material is arranged in layers of a thickness of 25-1,000 μm.

6. The model according to claim 1, characterized in that said supporting material is arranged in layers of a thickness of 50-500 μm.

7. The model according to claim 6, characterized in that said layers of supporting material are stacked.

8. The model according to claim 1, characterized in that said contrast material exhibits a solubility of at least 5 g·l$^{-1}$ at a temperature of 20° C. in a solvent.

9. The model according to claim 8, wherein said solvent is any one of water, ethanol, methanol, isopropanol, propanol, acetone, N-Methyl-2-pyrrolidone, dimethyl sulfoxide, dimethyl formamide, or acetonitrile.

10. The model according to claim 1, characterized in that said contrast material comprises an element with an atomic number of ≥19 with a weight portion of ≥0.01%.

11. The model according to claim 10, characterized in that said contrast material comprises an element with an atomic number of ≥19 selected from any one of iodine, lead, bromine, bismuth, stannic, antimony, gold, caesium, barium, rubidium, strontium, yttrium, zirconium, cerium, thorium, gadolinium, niobium, molybdenum, ruthenium, rhodium, palladium, silver, cadmium, indium, hafnium, or tantalum, with a weight portion of ≥0.01%.

12. A system comprising:
a model according to claim 1, and
a three-dimensional image of a human or animal body, wherein said three-dimensional image comprises a plurality of voxels, wherein each of said voxels has a spatial position, a volume element, and a voxel intensity, which represents an interaction intensity of a volume element of said body with an electromagnetic radiation measured by said imaging technique,
wherein each volume element of said model is allocated to a voxel of said three-dimensional image, and wherein said spatial position of each volume element of said model corresponds to said spatial position of said respective allocated voxel.

13. The system according to claim 12, characterized in that said model comprises at least a first set of second volume elements having an average interaction intensity and a second set of second volume elements having an average interaction intensity, wherein a ratio of the average interaction intensity of said first set of second volume elements to the average interaction intensity of said second set of second volume elements deviates from a ratio of an average voxel intensity of said voxels allocated to said volume elements of said first set to an average voxel intensity of said voxels allocated to said volume elements of said second set by ≤100%.

14. The system according to claim 13, wherein the ratio of the average interaction intensity of said volume elements of said first set to the average interaction intensity of said volume elements of said second set deviates from the ratio of the average voxel intensity of said voxels allocated to said volume elements of said first set to the average voxel intensity of said voxels allocated to said volume elements of said second set by ≤50%.

15. The system according to claim 13, wherein the ratio of the average interaction intensity of said volume elements of said first set to the average interaction intensity of said volume elements of said second set deviates from the ratio of the average voxel intensity of said voxels allocated to said volume elements of said first set to the average voxel intensity of said voxels allocated to said volume elements of said second set by ≤20%.

16. The system according to claim 13, wherein the ratio of the average interaction intensity of said volume elements of said first set to the average interaction intensity of said volume elements of said second set deviates from the ratio of the average voxel intensity of said voxels allocated to said volume elements of said first set to the average voxel intensity of said voxels allocated to said volume elements of said second set by ≤10%.

17. The system according to claim 12, characterized in that said interaction intensity of a volume element of said model measured by said imaging technique deviates from an average voxel intensity of a respective allocated voxel of said three-dimensional image by ≤100%.

18. The system according to claim 12, characterized in that said interaction intensity of a volume element of said model measured by said imaging technique deviates from an average voxel intensity of a respective allocated voxel of said three-dimensional image by ≤50%.

19. The system according to claim 12, characterized in that said interaction intensity of a volume element of said model measured by said imaging technique deviates from an average voxel intensity of a respective allocated voxel of said three-dimensional image by ≤15%.

20. The system according to claim 12, characterized in that each of said volume elements of said model comprises a portion of a contrast material comprising an amount of said contrast material, wherein said contrast material is characterized by a defined interaction with said electromagnetic radiation, on which said imaging technique is based, and wherein the amount of contrast material in said portion is proportional to said voxel intensity of said voxel allocated to said volume element.

* * * * *